[54] O-ALKYL-O-[1-CYANOALKYL-5-SUBSTITUTED-MERCAPTO-TRIAZOL(3)YL]-(THIONO)-PHOSPHORIC(PHOSPHONIC) ACID ESTERS OR ESTER-AMIDES

[75] Inventors: Hellmut Hoffmann, Wuppertal; Ingeborg Hammann, Cologne; Bernhard Homeyer, Opladen; Wilhelm Stendel, Wuppertal, all of Germany

[73] Assignee: Bayer Aktiengesellschaft, Leverkusen, Germany

[22] Filed: May 9, 1975

[21] Appl. No.: 576,074

[30] Foreign Application Priority Data

May 15, 1974 Germany............ 2423683

[52] U.S. Cl.............. 424/200; 260/308 R; 260/308 C; 260/454; 260/465.5 R; 260/959; 260/960
[51] Int. Cl.[2]............ A01N 9/36; C07F 9/65
[58] Field of Search............ 260/308 R; 424/200

[56] References Cited
FOREIGN PATENTS OR APPLICATIONS
2,301,400   7/1974   Germany................ 260/308 R Primary Examiner—Alton D. Rollins
Attorney, Agent, or Firm—Burgess, Dinklage & Sprung

[57] ABSTRACT

O-Alkyl-O-[1-cyanoalkyl-5-substituted-mercapto-triazol(3)yl]-(thiono)-phosphoric (phosphonic) acid esters or ester-amides of the formula

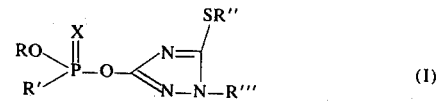

(I)

in which

R is alkyl with 1 to 6 carbon atoms,

R' is alkyl, alkoxy or alkylamino each with 1 to 6 carbon atoms, amino or phenyl, R'' is alkenyl with 2 to 6 carbon atoms, or alkyl, cyanoalkyl or alkylthioalkyl with 1 to 4 carbon atoms in each alkyl moiety, R''' is cyanoalkyl with 1 to 4 carbon atoms in the alkyl moiety, and X is oxygen or sulfur, which possess insecticidal, acaricidal and nematocidal properties.

10 Claims, No Drawings

O-ALKYL-O-[1-CYANOALKYL-5-SUBSTITUTED-MERCAPTO-TRIAZOL(3)YL]-(THIONO)-PHOSPHORIC(PHOSPHONIC) ACID ESTERS OR ESTER-AMIDES

The present invention relates to and has for its objects the provision of particular new O-alkyl-O-[1-cyanoalkyl-5-substituted-mercapto-triazol(3)yl]-(thiono)-phosphoric (phosphonic) acid esters or ester-amides, i.e. 5-alkylmercapto-, -alkenylmercapto-, -alkylthioalkylmercapto- and -cyanoalkylmercapto- compounds, which possess insecticidal, acaricidal and nematocidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It is known from U.S. Pat. No. 2,754,244 and German Published Specification DOS 2,259,960 that pyrazolylthionophosphoric acid esters, for example O,O-dimethyl-(Compound A) and O,O-diethyl-O-[3-methyl-pyrazol(5)yl]-thionophosphoric acid esters (Compound B) and triazolylthionophosphonic acid esters, for example O-ethyl-O-[1-isopropyl-5-methylthio-triazol(3)yl]-thionophenylphosphonic acid ester (Compound C) possess insecticidal and acaricidal properties.

The present invention provides O-triazolyl(thiono)-phosphoric(phosphonic) acid esters and ester-amides of the general formula

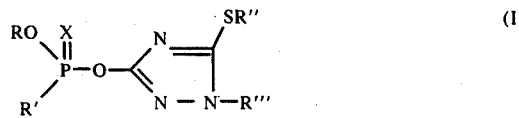

in which
R is alkyl with 1 to 6 carbon atoms,
R' is alkyl, alkoxy or alkylamino each with 1 to 6 carbon atoms, amino or phenyl,
R'' is alkenyl with 2 to 6 carbon atoms, or alkyl, cyanoalkyl or alkylthioalkyl with 1 to 4 carbon atoms in each alkyl moiety,
R''' is cyanoalkyl with 1 to 4 carbon atoms in the alkyl moiety, and
X is oxygen or sulfur.

Preferably, R is straight-chain or branched alkyl with 1 to 4 carbon atoms, R' is straight-chain or branched alkyl, alkoxy, monoalkylamino or dialkylamino with 1 to 4 carbon atoms in each alkyl moiety or amino or phenyl, R'' is straight-chain or branched alkyl or alkylthioalkyl with 1 to 3 carbon atoms in each alkyl moiety or alkenyl with 3 or 4 carbon atoms or cyanomethyl, 1-cyanoethyl or 2-cyanoethyl, and R''' is cyanomethyl, 1-cyanoethyl or 2-cyanoethyl.

Surprisingly, the O-triazolyl(thiono)-phosphoric(-phosphonic) acid esters and ester-amides according to the invention show a better insecticidal, acaricidal and nematocidal action than the previously known compounds of analogous structure and of the same type of action. At the same time, the new products are not only active against insects and mites which damage plants, but also in the veterinary medicine field against animal ectoparasites, for example parasitic fly larvae. They thus represent a genuine enrichment of the art.

The invention also provides a process for the preparation of an O-triazolyl(thiono)-phosphoric(phosphonic) acid ester or ester-amide of the formula (I) in which a (thiono)phosphoric (phosphonic) acid ester halide or ester-amide halide of the general formula

in which
R, R' and X have the abovementioned meanings and
Hal is halogen, preferably chlorine, is reacted with a triazolyl derivative of the general formula

in which
R'' and R''' have the abovementioned meanings, in the presence of an acid acceptor or in the form of an alkali metal salt, alkaline earth metal salt or ammonium salt.

If, for example, O-ethyl-thionophosphoric acid ester-amide chloride and 1-cyanomethyl-3-hydroxy-5-mehtylthio-1,2,4-triazole are used as starting materials, the course of the reaction can be represented by the following formula scheme:

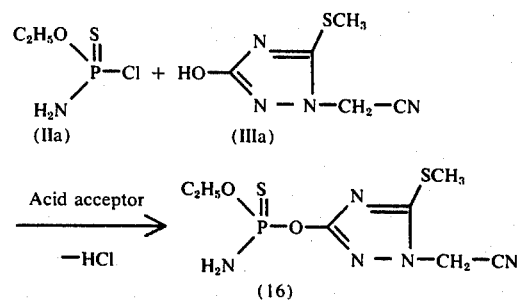

The formulae (II) and (III) provide an unambiguous general definition of the starting materials to be used.

The (thiono)-phosphoric(phosphonic) acid ester halide derivatives and ester-amide halide derivatives (II) are known from the literature and can be prepared according to customary processes.

The following may be mentioned individually as examples of these compounds: O,O-dimethyl-, O,O-diethyl-, O,O-di-n-propyl-, O,O-di-iso-propyl-, O,O-di-n-butyl-, O,O-di-isobutyl-, O,O-di-sec.-butyl-, O,O-di-tert.-butyl-, O-ethyl-O-n-propyl-, O-ethyl-O-iso-propyl-, O-n-butyl-O-ethyl-, O-ethyl-O-sec.-butyl- and O-ethyl-O-methyl-phosphoric acid diester chloride and the corresponding thiono analogues, as well as O-methyl-, O-ethyl-, O-n-propyl-, O-iso-propyl-, O-n-butyl-, O-sec.-butyl-, O-iso-butyl- and O-tert.-butyl-methane-, -ethane-, -n-propane-, -iso-propane-, -n-butane-, -isobutane-, -sec.-butane-, -tert.-butane- and -phenyl-phosphonic acid ester chloride and the corresponding thiono analogues, and also O-methyl-N-methyl-, O- ethyl-N-methyl-, O-n-propyl-N-methyl-, O-iso-propyl-N-methyl-, O-n-butyl-N-methyl-, O-sec.-butyl-N-methyl-, O-methyl-N-ethyl-, O-ethyl-N-ethyl-, O-n-propyl-N-ethyl-, O-iso-propyl-N-ethyl-, O-n-butyl-N-ethyl-, O-sec.-butyl-N-ethyl-, O-methyl-N-n-propyl-, O-ethyl-N-propyl-, O-n-propyl-N-n-propyl-, O-n-propyl-N-n-butyl-, o-iso-propyl-N-methyl-, O-iso-propyl-N-n-butyl- and O-tert.-butyl-N-ethyl-phosphoric acid ester-amide chloride, the corresponding dialkylamides, the free amides and the corresponding thiono analogues.

The new triazole derivatives of the formula (III) can be prepared according to customary processes, namely by reacting a cyanoalkylhydrazine with acetone and then with carbonic acid ethyl ester isothiocyanate (obtained from chloroformic acid ethyl ester and potassium thiocyanate) to give intermediate products of the following formula

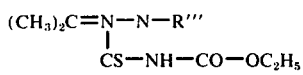

wherein

R''' has the abovementioned meaning, cyclizing the compounds of the formula (IV) and reacting them, for example, in accordance with the following equation, with a component of the formula R''Z, Z being a conveniently removable radical, for example halogen:

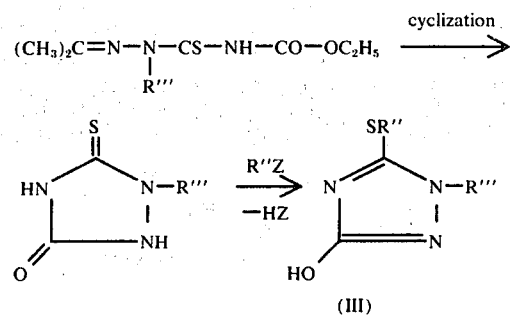

The following may be mentioned as examples of triazolyl derivatives (III): 1-cyanomethyl-, 1-(2'-cyanoethyl)- and 1-(1'-cyanoethyl)-3-hydroxy-5-methylthio-1,2,4-triazole, and also the corresponding -5-ethylthio-, -5-n-propylthio-, -5-iso-propylthio-, -5-n-butylthio-, -5-sec.-butylthio-, -5-tert.-butylthio-, -5-allylthio-, -5-buten(2)yl-thio-, -5-cyanomethylthio-, -5-(2'-cyanoethyl)-thio-, -5-(1'-cyanoethyl)-thio-, -5-methylthiomethylthio, -5-ethylthiomethylthio-, -5-ethylthioethylthio-, -5-ethylthiopropylthio-, -5-ethylthiobutylthio- and -5-propylthioethylthio derivatives.

The reaction of the process of the invention is preferably carried out in the presence of a solvent which term includes a mere diluent. Practically all inert organic solvents can be used for this purpose. These include, in particular, aliphatic and aromatic optionally chlorinated hydrocarbons, for example benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, for example acetonitrile and propionitrile.

All customary acid-binding agents can be used as the acid acceptor. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a substantial range. In general, the reaction is carried out at 0° to 130° C, preferably at 20° to 80° C.

The reaction is in general allowed to take place under normal pressure.

To carry out the process, the starting materials are in general employed in equimolar ratio. An excess of one or other component in general produces no significant advantages. The reaction is preferably carried out in the presence of one of the abovementioned solvents at the temperatures indicated. After a reaction time of one to several hours, in most cases at elevated temperatures, the batch may be cooled and the reaction mixture poured into water and taken up in an organic solvent, for example methylene chloride. The mixture may then be worked up in the usual manner by washing and drying the organic phase, evaporating the solvent and distilling the residue if appropriate. However, it is also possible to filter off the salt-like solids which have separated out after the end of the reaction time, evaporate off the solvent and distil the residue if appropriate.

Some of the new compounds are obtained in the form of oils which can in most cases not be distilled without decomposition but may be freed from the last volatile constituents by so-called "slight distillation", that is to say by prolonged heating under reduced pressure to moderately elevated temperatures, and may be purified in this way. They are characterized by the refractive index. Some of the compounds are obtained in a crystalline form having a sharp melting point.

As already mentioned, the O-triazolyl(thiono)-phosphoric(phosphonic) acid esters and ester-amides are distinguished by an excellent insecticidal, acaricidal and nematocidal activity. They are not only active against plant pests, hygiene pests and pests of stored products but also, in the veterinary medicine field, against animal parasites (ectoparasites), such as parasitic fly larvae. They combine a low phytotoxicity with a good action against both sucking and biting insects and mites. Some of the compounds also exhibit a soil-insecticidal action.

For this reason, the compounds according to the invention can be employed successfully as pesticides in plant protection and in the hygiene field, the field of protection of stored products and the veterinary field.

To the sucking insects there belong, in the main, aphids (Aphididae) such as the green peach aphid (*Myzus persicae*), the bean aphid (*Doralis fabae*), the bird cherry aphid (*Rhopalosiphum padi*), *the pea aphid* (*Macrosiphum pisi*) and the potato aphid (*Macrosiphum solanifolii*), the currant gall aphid (*Cryptomyzus korschelti*) the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) *and the soft scale* (*Lecanium hesperidum*) as well as the grape mealybug (*Pseudococcus maritimus*); thrips (Thysanoptera) such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma*

*infestans*) and, further, cicadas, such as *Euscelis bilobatus* and *Nephotettix bipunctatus*.

In the case of the biting insects, above all there should be mentioned bufferfly caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (Bruchidius = *Acanthoscelides obtectus*), the leather beetle (*Dermestes frischi*), the khapra bettle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain bettle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise esssentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*), and bluebottle fly (*Calliphora erythrocephala*), as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acari) there are classed, in particular, the spider mites (Tetranychidae) such as the two-spotted spider mite (*Tetranychus urticae*) and the European red mite (*Paratetranychus pilosus* = *Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against hygiene pests and pests of stored products, particularly flies and mosquitoes, the process products are also distinguished by an outstanding residual activity on wood and clay, as well as good stability to alkali on limed substrates.

The active compounds according to the invention couple a low toxicity to warm-blooded animals with powerful nematocidal properties and can therefore be used to combat nematodes, especially phytopathogenic nematodes. These essentially include leaf nematodes (Arphelenchoides), such as the chrysanthemum eelworm (*A. ritzemabosi*), the leaf-blotch eelworm (*A. fragariae*) and the rice eelworm (*A. oryzae*); stem nematodes (Ditylenchus); such as the stem eelworm (*D. Dipsaci*); root-knot nematodes (Meloidogyne), such as *M. arenaria* and *M. incognita*; cyst-forming nematodes (Heterodera), such as the potato cyst eelworm (*H. rostochiensis*) and the beet cyst eelworm (*H. schachtii*); and also free-living root nematodes, for example of the genera Pratylenchus, Paratylenchus, Rotylenchus, Xiphinema and Radopholus.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, expecially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arlypolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides and nematocides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001-10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. insects, acarids and nematodes, which comprises applying to at least one of correspondingly (a) such insects, (b) such acarids, (c) such nematodes, and (d) the corresponding habitat thereof, i.e. the locus to be protected, e.g. to a growing crop, to an area where a crop is to be grown or to a domestic animal, a correspondingly combative or toxic amount, i.e. an insecticidally, acaricidally or nematocidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in speciaal cases it is possible to go above or below the aforementioned concentration ranges.

The unexpected superiority and outstanding activity of the particular new compounds of the present invention are illustrated, without limitation, by the following examples:

EXAMPLE 1

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following Table 1:

Table 1

| (Myzus test) | | |
|---|---|---|
| Active compound | Active compound concentration in % by weight | Degree of destruction in % after 1 day |
| 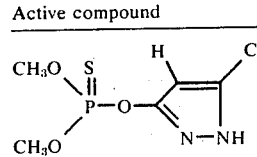 (A) | 0.1 | 0 |

Table 1-continued (*Myzus* test)

| Active compound | Active compound concentration in % by weight | Degree of destruction in % after 1 day |
|---|---|---|
| 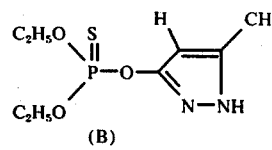 (B) | 0.1<br>0.01<br>0.001 | 99<br>40<br>0 |
| 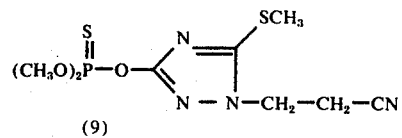 (9) | 0.1<br>0.01<br>0.001 | 100<br>100<br>75 |
| 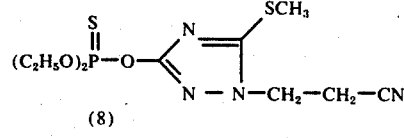 (8) | 0.1<br>0.01<br>0.001 | 100<br>100<br>99 |
| 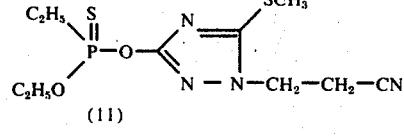 (11) | 0.1<br>0.01<br>0.001 | 100<br>100<br>60 |
| 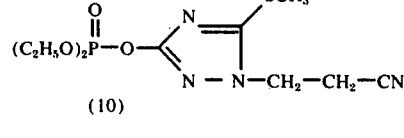 (10) | 0.1<br>0.01<br>0.001 | 100<br>100<br>70 |
| 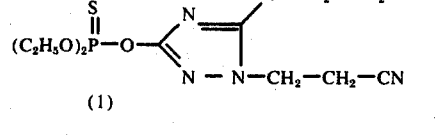 (1) | 0.1<br>0.01<br>0.001 | 100<br>95<br>60 |
| 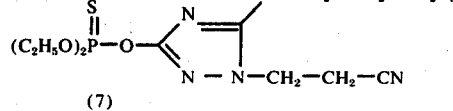 (7) | 0.1<br>0.01<br>0.001 | 100<br>100<br>80 |

EXAMPLE 2

Doralis test (systemic action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier, and the concentrate was diluted with water to the desired concentration.

Bean plants (*Vicia faba*) which had been heavily infested with the bean aphid (*Doralis fabae*) were watered with the preparation of the active compound so that the preparation penetrated into the soil without wetting the leaves of the bean plants. The active compound was taken up from the soil by the bean plants and thus passed to the infested leaves.

After the specified periods of time, the degree of destruction was determined as a precentage. 100% means that all the aphids were killed; 0% means that none of the aphids were killed.

The active compounds, the concentrations of the active compounds, the evaluation times and the results can be seen from the following Table 2:

Table 2

(Doralis test/systemic action)

| Active compound | Active compound concentration in % by weight | Degree of destruction in % after 4 days |
|---|---|---|
| (A) CH₃O-P(=S)(OCH₃)-O-C(H)=C(CH₃)-N=NH pyrazole | 0.1 | 0 |
| (C) C₂H₅O-P(=S)(C₆H₅)-O-C(SCH₃)=C-N=N-C₃H₇i | 0.1 | 0 |
| (9) (CH₃O)₂P(=S)-O-C(SCH₃)=C-N=N-CH₂-CH₂-CH | 0.1 | 100 |
| (8) (C₂H₅O)₂P(=S)-O-C(SCH₃)=C-N=N-CH₂-CH₂-CN | 0.1 | 100 |
| (11) (C₂H₅)(C₂H₅O)P(=S)-O-C(SCH₃)=C-N=N-CH₂-CH₂-CN | 0.1 | 100 |
| (10) (C₂H₅O)₂P(=O)-O-C(SCH₃)=C-N=N-CH₂-CH₂-CN | 0.1 | 100 |
| (12) iso-C₃H₇-HN,(C₂H₅O)P(=S)-O-C(SCH₃)=C-N=N-CH₂-CH₂-CN | 0.1 | 100 |
| (3) (C₂H₅O)₂P(=S)-O-C(S-CH₂-CN)=C-N=N-CH₂-CH₂-CN | 0.1 | 100 |
| (14) (C₂H₅)(C₂H₅O)P(=S)-O-C(S-CH₂-CN)=C-N=N-CH₂-CH₂-CN | 0.1 | 100 |
| (15) (C₂H₅O)₂P(=O)-O-C(S-CH₂-CN)=C-N=N-CH₂-CH₂-CN | 0.1 | 100 |
| (1) (C₂H₅O)₂P(=S)-O-C(S-CH₂-CH₂-CN)=C-N=N-CH₂-CH₂-CN | 0.1 | 100 |

EXAMPLE 3

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the common or two-spotted spider mite (*Tetranychus urticae*) in all stages of development.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following Table 3:

Table 3

(Tetranychus test/resistant)

| Active Compound | Active compound concentration in % by weight | Degree of destruction in % after 2 days |
| --- | --- | --- |
| (A) | 0.1 | 0 |
| (9) | 0.1 | 100 |
| (8) | 0.1 | 100 |
| (11) | 0.1 | 100 |
| (10) | 0.1 | 100 |
| (2) | 0.1 | 99 |
| (3) | 0.1 | 99 |
| (14) | 0.1 | 100 |
| (13) | 0.1 | 100 |

EXAMPLE 4

Test with parasitic fly larvae

Solvent: 35 parts by weight of ethylene polyglycol monomethyl ether
35 parts by weight of nonylphenol polyglycol ether To produce a suitable preparation of active compound, 30 parts by weight of the active substance in question were mixed with the stated amount of solvent which contained the abovementioned proportion of emulsifier and the concentrate thus obtained was diluted with water to the desired concentration.

About 20 fly larvae (*Lucilia cuprina*), were introduced into a test tube which contained approximately 2 cm³ of horse muscle. 0.5 ml of the preparation of active compound was applied to this horse meat. After 24 hours, the degree of destruction in % was determined. 100% means that all larvae had been killed and 0% means that no larvae had been killed.

The active compounds investigated, the concentrations of the active compounds used and the results obtained can be seen from Table 4 which follows:

Table 4

| Active compound | Active compound concentration in ppm | Degree of destruction in % (Lucilia cuprina/resistant) |
|---|---|---|
| (8) $(C_2H_5O)_2P(S)-O-$ [ring with SCH₃, N−N−CH₂−CH₂−CN] | 100<br>30<br>10<br>3<br>1 | 100<br>—<br>100<br>—<br>>50 |
| (9) $(CH_3O)_2P(S)-O-$ [ring with SCH₃, N−N−CH₂−CH₂−CN] | 100<br>30<br>10<br>—<br>— | 100<br>100<br>100<br>—<br>— |
| (10) $(C_2H_5O)_2P(O)-O-$ [ring with SCH₃, N−N−CH₂−CH₂−CN] | 100<br>30<br>10<br>— | 100<br>—<br>100<br>— |
| (11) $C_2H_5,C_2H_5O-P(S)-O-$ [ring with SCH₃, N−N−CH₂−CH₂−CN] | 100<br>30<br>10<br>— | 100<br>—<br>>50<br>— |
| (13) $(C_2H_5O)_2P(S)-O-$ [ring with S−CH₂−CH=CH₂, N−N−CH₂−CH₂−CN] | 100<br>30<br>10<br>— | 100<br>100<br>>50<br>— |
| (15) $(C_2H_5O)_2P(O)-O-$ [ring with S−CH₂−CN, N−N−CH₂−CH₂−CN] | 100<br>30<br>10<br>— | 100<br>—<br>>50<br>— |
| (3) $(C_2H_5O)_2P(S)-O-$ [ring with S−CH₂−CN, N−N−CH₂−CH₂−CN] | 100<br>30<br>10<br>— | 100<br>—<br>>50<br>— |
| (4) iso-$C_3H_7$−HN, $C_2H_5O$−P(O)−O− [ring with S−CH₂−CH=CH₂, N−N−CH₂−CH₂−CN] | 100<br>30<br>10<br>— | 100<br>—<br>100<br>— |
| (1) $(C_2H_5O)_2P(S)-O-$ [ring with S−CH₂−CH₂−CN, N−N−CH₂−CH₂−CN] | 100<br>30<br>10<br>— | 100<br>—<br>>50<br>— |

EXAMPLE 5

Critical concentration test
Test nematode: *Meloidogyne incognita*
Solvent: 3 parts by weight of acetone Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given in ppm, was decisive. The treated soil was filled with pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compounds, the amounts applied and the results can be seen from the following Table 5:

Table 5

Critical concentration test/nematodes (*Meloidogyne incognita*)

| Active compound | Degree of destruction in % at an active compound concentration of 20 ppm |
|---|---|
| (A) | 0 |
| (B) | 0 |
| (C) | 0 |
| (8) | 100 |
| (11) | 100 |
| (12) | 100 |
| (13) | 100 |
| (14) | 100 |

Table 5-continued

Critical concentration test/nematodes (*Meloidogyne incognita*)

| Active compound | Degree of destruction in % at an active compound concentration of 20 ppm |
|---|---|
|  (3) | 100 |
|  (1) | 100 |
| 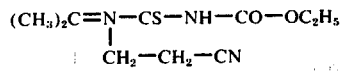 (7) | 100 |

EXAMPLE 6:

a. The triazole derivatives (III) used as starting materials were prepared, for example, as follows:

$$C_2H_5O-CO-N=C=S \quad \text{(i)}$$

218 g of freshly distilled chloroformic acid ethyl ester were added to 200 g (2 mols) of potassium thiocyanate in 800 ml of acetone at 60°–70° C and the mixture was stirred for 2 hours. The solids which had been separated out were then filtered off, the solvent was evaporated off and the residue was distilled at 55° C and 12 mm Hg. 84 g (32% of theory) of carbonic acid ethyl ester isothiocyanate were obtained.

$$NC-CH_2-CH_2-NH-NH_2 \quad \text{(ii)}$$

106 g of acrylonitrile were added dropwise to 110 g (2 moles) of 80% strength hydrazine in 50 ml of water at 0°–5° C, volatile materials were evaporated off at a bath temperature of 35°–40° C and the residue was distilled at 100° C/4 mm Hg. 134 g (79% of theory) of 2-cyanoethylhydrazine were obtained.

$$(CH_3)_2C=N-CS-NH-CO-OC_2H_5 \quad \text{(iii)}$$
$$\quad\quad\quad\quad\;\; |$$
$$\quad\quad\quad\;\; CH_2-CH_2-CN$$

85 g of the freshly distilled compound described under (ii) were added dropwise to 300 ml of acetone, the reaction temperature of the mixture was kept at 30°–40° C and stirring was continued for a further 2 hours. 131 g of the compound described under (i) were then added at 30°–35° C, the mixture was stirred for 2 hours and evaporated and the residue was recrystallized from an ethyl acetate/ligroin mixture. 187 g (73% of theory) of the desired compound, of melting point 80° C, were obtained.

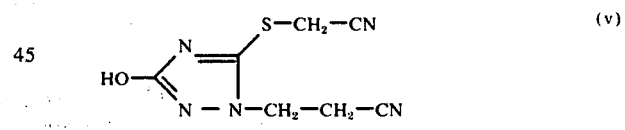

A mixture of 200 ml of water, 26 g (0.1 mole) of the product described under (iii) and 10 ml of hydrochloric acid was heated to approximately 65° C until a clear solution was obtained and was then cooled and the solids present were filtered off and recrystallized from water. 12 g (70% of theory) of 1-(2'-cyanoethyl)-3-oxo-5-thiono-triazolidine-(1,2,4) of melting point 115°–118° C (with decomposition) were obtained.

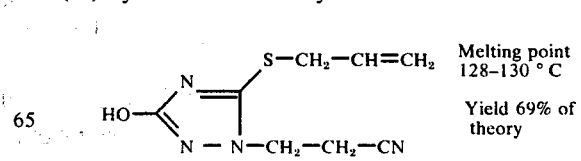

38 g of chloroacetonitrile were added to a mixture of 85 g (0.5 mole) of the product described under (iv), 400 ml of methanol and an 0.5 molar sodium methylate solution at 50°–60° C and this mixture was stirred for a further 3 hours at 50°–60° C. The solvent was then evaporated off and the residue was triturated with water, filtered off and dried on clay. 63 g (60% of theory) of 1-(2'-cyanoethyl)-3-hydroxy-5-cyanomethyl-triazole-(1,2,4) of melting point 180°–185° C were obtained.

The following compounds were obtained analogously : (vi) by reaction with allyl bromide:

Melting point 128–130 °C

Yield 69% of theory (vii) by reaction with 2-chloroethyl ethyl thioether

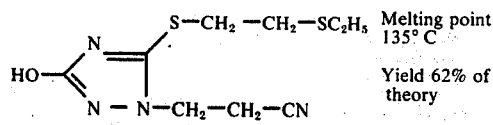 Melting point 135° C
Yield 62% of theory (viii) by reaction with 2-bromo-propionitrile

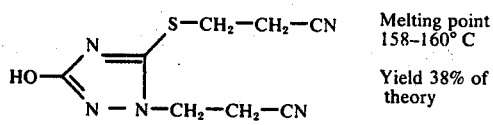 Melting point 158–160° C
Yield 38% of theory (ix)

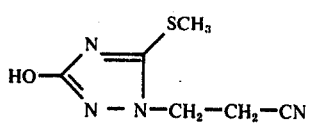

17 g (0.1 mol) of the compound described under (iv), followed by 13 g of dimethyl sulfate, were added to 50 ml of water and 4 g of sodium hydroxide, the reaction temperature being kept at 30°–35° C. After stirring for two hours, the solid which had separated out was filtered off, dried and recrystallized from methanol. 12 g (65% of theory) of 1-(2'-cyanoethyl)-3-hydroxy-5-methylthio-triazole-(1,2,4) of melting point 193° C were obtained.

(b)

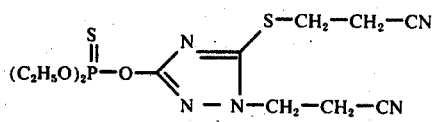 (1)

19 g of O,O-diethylthionosphosphoric acid diester chloride were added to a mixture of 22 g (0.1 mole) of 1-(2'-cyanoethyl)-3-hydroxy-5-(2'-cyanoethylmercapto)-triazole-(1,2,4) (produced as described in (a) (VIII) hereinabove) in 200 ml of acetonitrile and 15 g of potassium carbonate and the mixture was stirred for 4 hours at 80° C. Thereafter the reaction mixture was poured into water and extracted by shaking with methylene chloride, and the solvent was distilled off in vacuo after washing and drying the organic phase. After the residue had been subjected to slight distillation, it solidified and was recrystallized from an ethyl acetate/ligroin mixture. 15 g (38% of theory) of O,O-diethyl-O-[1-(2'-cyanoethyl)-5-(2'-cyanoethylmercapto)-triazol(3)yl]-thionophosphoric acid ester of melting point 73°–76° C were obtained.

EXAMPLE 7

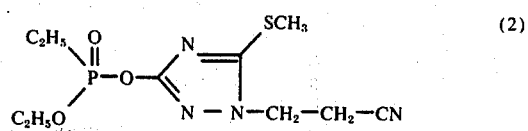 (2)

17 g of O-ethyl-ethanephosphonic acid ester chloride were added to a mixture of 19 g (0.1 mole) of 1-(2'-cyanoethyl)-3-hydroxy-5-methylmercapto-triazole-(1,2,4 (produced as described in (a) (ix) hereinabove) in 200 ml of acetonitrile and 15 g of potassium carbonate and the mixture was stirred for 4 hours at 40°–45° C. Thereafter, salt-like solids were filtered off, the solvent was evaporated off in vacuo and the residue was subjected to incipient distillation. 20 g (66% of theory) of O-ethyl-O-[1-(2'-cyanoethyl)-5-methylmercapto-triazol(3)yl]-ethanephoshonic acid ester of refractive index $n_D^{20}$: 1.5080 were obtained.

The following compounds were prepared analogously:

| Compound | Structure | Physical data (refractive index, melting point) |
|---|---|---|
| 3 | (C₂H₅O)₂P(S)–O–[triazole]–S–CH₂–CN, N–N–CH₂–CH₂–CN | $n_D^{21}$: 1.5255 |
| 4 | iso-C₃H₇–HN, C₂H₅O, P(O)–O–[triazole]–S–CH₂–CH=CH₂, N–N–CH₂–CH₂–CN | $n_D^{21}$: 1.5114 |
| 5 | C₆H₅, C₂H₅O, P(S)–O–[triazole]–S–CH₂–CH₂–CN, N–N–CH₂–CH₂–CN | $n_D^{20}$: 1.5750 |
| 6 | C₂H₅O, H₂N, P(S)–O–[triazole]–SCH₃, N–N–CH₂–CH₂–CN | $n_D^{21}$: 1.5575 |

-continued

| Compound | Structure | Physical data (refractive index, melting point) |
|---|---|---|
| 7 | (C$_2$H$_5$O)$_2$P(=S)—O—[ring: N=C(S—CH$_2$—CH$_2$—SC$_2$H$_5$)—N—N—CH$_2$—CH$_2$—CN] | $n_D^{22}$: 1.5360 |
| 8 | (C$_2$H$_5$O)$_2$P(=S)—O—[ring: N=C(SCH$_3$)—N—N—CH$_2$—CH$_2$—CN] | $n_D^{29}$: 1.5212 |
| 9 | (CH$_3$O)$_2$P(=S)—O—[ring: N=C(SCH$_3$)—N—N—CH$_2$—CH$_2$—CN] | $n_D^{21}$: 1.5356 |
| 10 | (C$_2$H$_5$O)$_2$P(=O)—O—[ring: N=C(SCH$_3$)—N—N—CH$_2$—CH$_2$—CN] | $n_D^{21}$: 1.4952 |
| 11 | C$_2$H$_5$(C$_2$H$_5$O)P(=S)—O—[ring: N=C(SCH$_3$)—N—N—CH$_2$—CH$_2$—CN] | $n_D^{21}$: 1.5380 |
| 12 | iso-C$_3$H$_7$—HN(C$_2$H$_5$O)P(=S)—O—[ring: N=C(SCH$_3$)—N—N—CH$_2$—CH$_2$—CN] | M.p. 68° C |
| 13 | (C$_2$H$_5$O)$_2$P(=S)—O—[ring: N=C(S—CH$_2$—CH=CH$_2$)—N—N—CH$_2$—CN] | $n_D^{21}$: 1.5269 |
| 14 | C$_2$H$_5$(C$_2$H$_5$O)P(=S)—O—[ring: N=C(S—CH$_2$—CN)—N—N—CH$_2$—CH$_2$—CN] | $n_D^{21}$: 1.5450 |
| 15 | (C$_2$H$_5$O)$_2$P(=O)—O—[ring: N=C(S—CH$_2$—CN)—N—N—CH$_2$—CH$_2$—CN] | $n_D^{21}$: 1.5030 |

Other compounds which can be similarly prepared include:

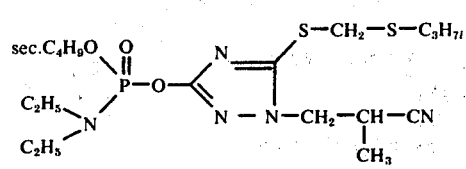

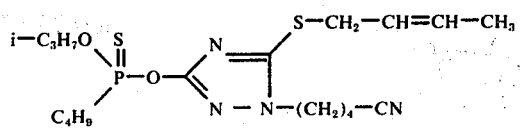

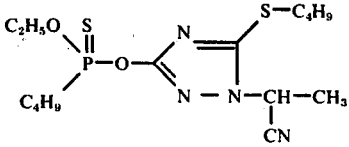

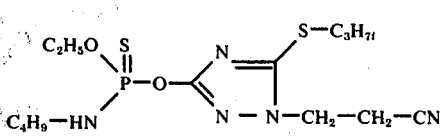

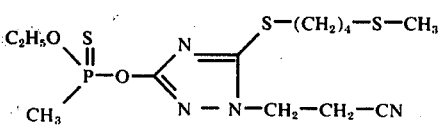

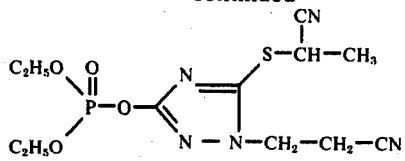

and the like.

It will be appreciated that the instant specification and examples are set forth by way of illustration and not limitation, and that various modifications and changes may be made without departing from the spirit and scope of the present invention.

What we claim is:

1. An-O-alkyl-O-[1-cyanoalkyl-5-substituted-mercapto-triazol-(3)yl]-(thiono)-phosphoric(phosphonic) acid ester or esteramide of the formula

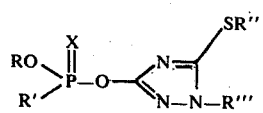

in which
R is alkyl with 1 to 6 carbon atoms,
R' is alkyl, alkoxy or alkylamino each with 1 to 6 carbon atoms, amino or phenyl,
R'' is alkenyl with 2 to 6 carbon atoms, or alkyl, cyanoalkyl or alkylthioalkyl with 1 to 4 carbon atoms in each alkyl moiety,
R''' is cyanoalkyl with 1 to 4 carbon atoms in the alkyl moiety, and
X is oxygen or sulfur.

2. A compound according to claim 1 in which R is alkyl with 1 – 4 carbon atoms, R' is alkyl, alkoxy, monoalkylamino or dialkylamino with 1-4 carbon atoms in each alkyl moiety, amino or phenyl, R'' is alkyl or alkylthioalkyl with 1-3 carbon atoms in each alkyl moiety, alkenyl with 3 or 4 carbon atoms or cyanomethyl, 1-cyanoethyl or 2-cyanoethyl, and R''' is cyanomethyl, 1-cyanoethyl or 2-cyanoethyl.

3. A compound according to claim 1, wherein such compound is O,O-diethyl-O-[1-(2'-cyanoethyl)-5-methylmercapto-traizol-(3)yl]-thionophoshoric acid ester of the formula

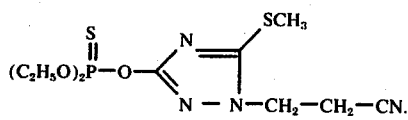

4. A compound according to claim 1, wherein such compound is O,O-dimethyl-O-[1-(2'-cyanoethyl)-5-methylmercapto-triazol(3)yl]-thionophoshoric acid ester of the formula

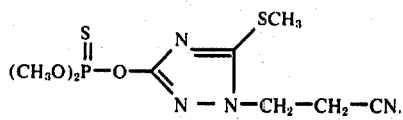

5. A compound according to claim 1, wherein such compound is O,O-diethyl-O-[1-(2'-cyanoethyl)-5-methylmercapto-triazol-(3)yl]-phosphoric acid ester of the formula

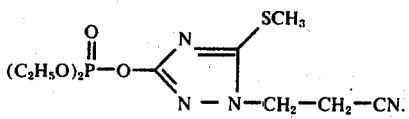

6. A compound according to claim 1, wherein such compound is O-ethyl-O-[1-(2'-cyanoethyl)-5-methylmercapto-triazol-(3)yl]-ethanethionophosphonic acid ester of the formula

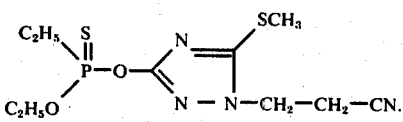

7. A compound according to claim 1, wherein such compound is O,O-diethyl-O-[1-(2'-cyanoethyl)-5-allylmercapto-triazol-(3)yl]-thionophosphoric acid ester of the formula

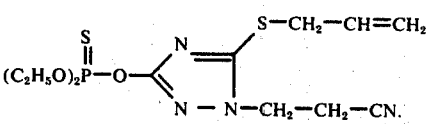

8. An insecticidal, acaricidal or nematocidal composition containing as active ingredient an insecticidally, acaricidally or nematocidally effective amount of a compound according to claim 1 in admixture with a diluent.

9. A method of combating insect, acarid or nematode pests which comprises applying to the pests or a habitat thereof an insecticidally, acaracidally or nematocidally effective amount of a compound according to claim 1.

10. The method according to claim 9 in which said compound is O,O-diethyl-O-[1-(2'-cyanoethyl)-5-methylmercapto-triazol(3)yl]-thionophosphoric acid ester, O,O-dimethyl-O-[1-(2'-cyanoethyl)-5-methylmercapto-triazol(3)]-thionophoshoric acid ester, O,O-diethyl-O-[1-(2'-cyanoethyl)-5-methylmercapto-triazol(3)yl]-phosphoric acid ester, O-ethyl-O-[1-(2'-cyanoethyl)-5-methylmercapto-triazol(3)yl]-ethanethionophosphonic acid ester, or O,O-diethyl-O-[1-(2'-cyanoethyl)-5-allylmercapto-triazol(3)yl]-thionophosphoric acid ester.

* * * * *

Disclaimer 3,987,168.—*Hellmut Hoeffmann*, Wuppertal, *Ingeborg Hammann*, Cologne, *Bernhard Homeyer*, Opladen, and *Wilhelm Stendel*, Wuppertal, Germany. O-ALKYL-O-[1-CYANOALKYL-5-SUBSTITUTED-MERCAPTO - TRIAZOL(3)YL]-(THIONO)-PHOSPHORIC(PHOSPHONIC) ACID ESTERS OR ESTER-AMIDES. Patent dated Oct. 19, 1976. Disclaimer filed Feb. 14, 1977, by the assignee, *Bayer Aktiengesellschaft*.

Hereby enters this disclaimer to claims 1, 2, 4 and 6 to 10 of said patent.

[*Official Gazette April 12, 1977.*]